(12) United States Patent
Buhot et al.

(10) Patent No.: US 8,664,595 B2
(45) Date of Patent: Mar. 4, 2014

(54) CLUSTER ANALYSIS OF UNKNOWNS IN SEM-EDS DATASET

(75) Inventors: Michael Buhot, Brisbane (AU); Van Hung Phan, Chapel Hill (AU); Michael James Owen, Geebung (AU)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 13/536,308

(22) Filed: Jun. 28, 2012

(65) Prior Publication Data

US 2014/0001356 A1 Jan. 2, 2014

(51) Int. Cl.
*G21K 7/00* (2006.01)

(52) U.S. Cl.
CPC ................................. *G21K 7/00* (2013.01)
USPC .............................. 250/306; 250/307; 378/49

(58) Field of Classification Search
USPC .................................... 250/306, 307; 378/49
See application file for complete search history.

(56) References Cited

U.S. PATENT DOCUMENTS

| | | | |
|---|---|---|---|
| 4,037,101 A | 7/1977 | Okumura et al. | |
| 4,136,429 A | 1/1979 | Brandes | |
| 4,242,586 A | 12/1980 | Warble | |
| 4,435,507 A | 3/1984 | Stenkvist | |
| 4,476,386 A | 10/1984 | Reid et al. | |
| 4,592,082 A | 5/1986 | Pawloski | |
| 4,807,148 A | 2/1989 | Lacey | |
| 4,834,943 A | 5/1989 | Yoshiyama | |
| 4,839,516 A | 6/1989 | Freeman et al. | |
| 5,084,618 A | 1/1992 | Ito | |
| 5,555,198 A | 9/1996 | Asano | |
| RE35,514 E | 5/1997 | Albrecht et al. | |
| 5,741,707 A | 4/1998 | Herron et al. | |
| 5,798,525 A | 8/1998 | Benizri-Carl et al. | |
| 5,866,903 A | 2/1999 | Morita et al. | |
| 5,906,919 A | 5/1999 | Garini et al. | |
| 5,991,028 A | 11/1999 | Cabib et al. | |
| 6,018,587 A | 1/2000 | Cabib | |
| 6,066,459 A | 5/2000 | Garini et al. | |

(Continued)

FOREIGN PATENT DOCUMENTS

| | | |
|---|---|---|
| CN | 100498309 | 6/2009 |
| JP | 05087707 | 4/1993 |

(Continued)

OTHER PUBLICATIONS

Pye, et al., "Forensic Geoscience: Principles, Techniques and Applications," The Geological Society, Mar. 3 & 4, 2003, 55 pages.

(Continued)

*Primary Examiner* — Kiet T Nguyen
(74) *Attorney, Agent, or Firm* — Scheinberg & Associates, PC; Michael O. Scheinberg

(57) ABSTRACT

The present invention discloses a method for determining the mineral content represented by the entire SEM-EDS dataset, including initially unknown data points. SEM-EDS data points are taken and compared to a set of known data points. Any data point that is not sufficiently similar to the known data point is classified as unknown and clustered with like unknown data points. After all data points are analyzed, any clusters of unknown data points with a sufficient number of data points are further analyzed to determine their characteristics. All clusters of unknown data points with an insufficient number of data points to allow further analysis are considered outliers and discarded.

14 Claims, 9 Drawing Sheets

(56) References Cited

U.S. PATENT DOCUMENTS

| | | | |
|---|---|---|---|
| 6,072,178 A | 6/2000 | Mizuno | |
| 6,093,930 A | 7/2000 | Boyette, Jr. et al. | |
| 6,122,343 A | 9/2000 | Pidcock | |
| 6,140,643 A * | 10/2000 | Brown et al. | 850/10 |
| 6,282,301 B1 | 8/2001 | Haskett | |
| 6,341,257 B1 | 1/2002 | Haaland | |
| 6,377,652 B1 | 4/2002 | Sturm | |
| 6,466,929 B1 | 10/2002 | Brown et al. | |
| 6,470,335 B1 | 10/2002 | Marusak | |
| 6,584,413 B1 | 6/2003 | Keenan et al. | |
| 6,658,143 B2 | 12/2003 | Hansen et al. | |
| 6,674,894 B1 | 1/2004 | Parker et al. | |
| 6,687,620 B1 | 2/2004 | Haaland et al. | |
| 6,711,503 B2 | 3/2004 | Haaland et al. | |
| 6,723,871 B2 | 4/2004 | Tada et al. | |
| 6,724,940 B1 | 4/2004 | Qian et al. | |
| 6,765,205 B2 | 7/2004 | Ochiai et al. | |
| 6,842,702 B2 | 1/2005 | Haaland et al. | |
| 6,888,920 B2 | 5/2005 | Blank et al. | |
| 6,977,723 B2 | 12/2005 | Lemmo et al. | |
| 6,993,170 B2 | 1/2006 | Johnson et al. | |
| 7,061,605 B2 | 6/2006 | Lemmo et al. | |
| 7,108,970 B2 | 9/2006 | Levinson | |
| 7,132,652 B1 | 11/2006 | Testoni | |
| 7,139,415 B2 | 11/2006 | Finkbeiner | |
| 7,161,672 B2 | 1/2007 | Gornushkin et al. | |
| 7,243,030 B2 | 7/2007 | Reeve et al. | |
| 7,400,770 B2 | 7/2008 | Keaton et al. | |
| 7,436,510 B2 | 10/2008 | Grun et al. | |
| 7,490,009 B2 | 2/2009 | Gottlieb et al. | |
| 7,790,465 B2 | 9/2010 | Otvos | |
| 7,930,106 B2 | 4/2011 | Carrick | |
| 7,979,217 B2 | 7/2011 | Gottlieb et al. | |
| 8,060,173 B2 | 11/2011 | Goode, Jr. et al. | |
| 2002/0169589 A1 | 11/2002 | Banki et al. | |
| 2004/0011958 A1 | 1/2004 | Wright et al. | |
| 2004/0027350 A1 | 2/2004 | Kincaid et al. | |
| 2004/0099805 A1 | 5/2004 | Ochiai et al. | |
| 2004/0147830 A1 | 7/2004 | Parker et al. | |
| 2005/0037515 A1 | 2/2005 | Nicholson et al. | |
| 2005/0060868 A1 | 3/2005 | McMurtry | |
| 2005/0165290 A1 | 7/2005 | Kotsianti et al. | |
| 2006/0051251 A1 | 3/2006 | Desrosiers et al. | |
| 2006/0291619 A1 | 12/2006 | Statham | |
| 2007/0279629 A1 | 12/2007 | Grun et al. | |
| 2008/0137082 A1 | 6/2008 | Grun et al. | |
| 2008/0250881 A1 | 10/2008 | Dona | |
| 2010/0060893 A1 | 3/2010 | Norton et al. | |
| 2011/0144922 A1 | 6/2011 | Corbett et al. | |
| 2011/0301869 A1 | 12/2011 | Gottlieb et al. | |
| 2013/0015351 A1 | 1/2013 | Kooijman et al. | |
| 2013/0134307 A1 | 5/2013 | Routh, Jr. | |

FOREIGN PATENT DOCUMENTS

| | | |
|---|---|---|
| JP | 08015185 | 1/1996 |
| JP | 1031273 | 2/1998 |
| JP | 2000249608 | 9/2000 |
| JP | 2001006597 | 1/2001 |
| JP | 2001066269 | 3/2001 |
| JP | 2002189005 | 7/2002 |
| JP | 2011113640 | 6/2011 |
| RU | 2054660 | 2/1996 |
| WO | 9905503 | 2/1999 |
| WO | 2008013597 | 1/2008 |
| WO | 2009100404 | 8/2009 |

OTHER PUBLICATIONS

Pye, et al., "Forensic Geoscience: Principles, Techniques and Applications," The Geological Society, 2004, 26 pages.
Unknown, "Raith e_Line User Guide," online, Nov. 2009, 18 pages.
Slocum, Alexander, "Design of three-groove kinematic couplings," Precision Engineering, Apr. 1992, pp. 67-77, vol. 14, No. 2.
Slocum, Alexander, "Kinematic couplings for precision fixturing—Part I: Formulation of design parameters," Precision Engineering, Apr. 1988, pp. 85-92, vol. 10 No. 2.
Slocum, et al., "Kinematic couplings for precision fixturing—Part 2: Experimental determination of repeatability and stiffnes," Precision Engineering, Jul. 1988, pp. 115-122, vol. 10 No. 3.
Slocum, Alexander, "Kinematic couplings: a review of design principles and applications," International Journal of Machine Tools & Manufacture, 2010, pp. 310-327, vol. 50.
Sutherland, et al., "Application of Automated Quantitative Mineralogy in Mineral Processing," Minerals Engineering, 1991, pp. 753-762, vol. 4 No. 7-11.
Sutherland, David, "Image Analysis for Off-Line Characterisation of Mineral Particles and Prediction of Processing Properties," Part. Part. Syst. Charact., 1993, pp. 271-274, vol. 10.
Van Hoek, Corrie, J.G., et al., "A SEM-EDS Study of Cultural Heritage Objects with Interpretation of Constituents and Their Distribution Using PARC Data Analysis," Microsc. Microanal. 2011, pp. 656-660, vol. 17.
Zelenika, S., et al., "Kinematic Couplings for Synchroton Radiation Instrumentation," 2nd International Workshop on Mechanical Engineering Design of Synchrotron Radiation Equipment and Instrumentation, Sep. 5-6, 2002, 9 pages.
Ashton, Edward A., et al., "Multialgorithm Solution for Automated Multispectral Target Detection," Opt. Eng., Apr. 1999, pp. 717-724, vol. 38, No. 4.
Benz, Ursula C., et al., "Multi-resolution, Object-oriented Fuzzy Analysis of Remote Sensing Data for GIS-ready Information," ISPRS Journal of Photogrammetry & Remote Sensing, 2004, pp. 239-258, vol. 58.
Creelman, Robert A., et al., "A Scanning Electron Microscope Method for Automated, Quantitative Analysis of Mineral Matter in Coal," International Journal of Coal Geology, 1996, pp. 249-269, vol. 30.
Unknown, "Energy-dispersive X-ray spectroscopy," Wikepedia, http://en.wikipedia.org/wiki/Engergy_Dispersive_Spectroscopy, obtained Jul. 29, 2013.
Fandrich, Rolf, et al., "Modern SEM-based mineral liberation alaysis," Int. J. Miner. Process., 2007, 310-320, vol. 84.
Figueroa, German, et al., "Advanced discrimination of hematite and magnetite by automated mineralogy," 10th International Congress for Applied Mineralogy, Aug. 1-5, 2011, pp. 197-204.
Furse, J.E., "Kinematic design of fine mechanisms in instruments," J. Phys. E: Sci. Instrum, 1981, pp. 264-272, vol. 14.
Ghassemian, Hassan, et al., "Object-Oriented Feature Extraction Method for Image Data Compaction," IEEE Control Systems Magazine, Jun. 1998, pp. 42-48.
Gottlieb, P., et al., "The Automatic Identification and Quantification of Silver Minerals," XVIII International Mineral Processing Congress, May 23-28, 1993, pp. 475-481, Sydney, Australia.
Gottlieb, P. et al., "Using Quantitative Electron Microscopy for Process Mineralogy Applications," Microtextural Mineralogy, Apr. 2000, pp. 24-25.
Gu, Ying, "Automated Scanning Electron Microscope Based Mineral Liberation Analysis, An Introduction to JKMRC/FEI Mineral Liberation Analyser," Journal of Mineral & Materials Characterization & Engineering, 2003, pgs. 33-41, vol. 2, No. 1.
Hale, Layton C., et al., "Optimal design techniques for kinematic couplings," Journal of the International Societies for Precision Engineering and Nanotechnology, Oct. 5, 2000, pp. 114-127, vol. 25.
Hazel, Geoffrey G., "Object-level Processing of Spectral Imagery for Detection of Targets and Changes Using Spatial-Spectral-Temporal Techniques," Proceeding of the SPIE, 2001, pp. 380-390, vol. 4381.
Jana, Dipayan, "Sample preparation techniques in a petrographic examinations of construction materials; a state-of-the-art review," Proceedings of the twenty-eighth Conference on Cement Microscopy, Apr. 30-May 4, 2006, pp. 48.
Lapicki, Adam, et al., "Kinematic sample mounting system for accurate positioning of transferrable samples," J. Vac. Sci. Technol., Sec. A, Sep./Oct. 2000, pp. 2603-2605, vol. 18 (5).
Meyer, K., et al., "Qualitative and Quantitative Mixture Analysis by Library Search: Infrared Analysis of Mixtures of Carbohydrates," Analytica Chimica Acta, Sep. 1, 1993, pp. 161-171, vol. 161-171.

(56) References Cited

OTHER PUBLICATIONS

Newbury, Dale E., "Chemical Compositional Mapping by Microbeam Analysis at the Micrometer Scale and Finer," Microelectronics Journal, 1997. pp. 489-508, vol. 28.

Newbury, Dale E., "Pushing the Envelope with SEM/SDD-EDS Mapping: X-ray Spectrum Image Mapping in 30 Seconds or Less, But What are the Real Limits?" Proc. of SPIE, 2010, p. 9, vol. 7729.

* cited by examiner

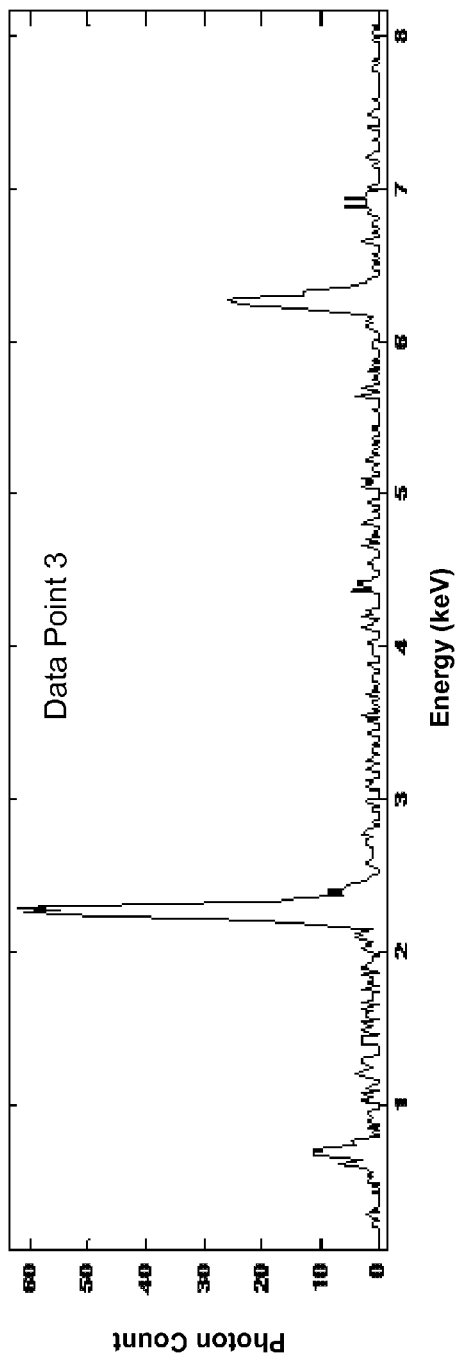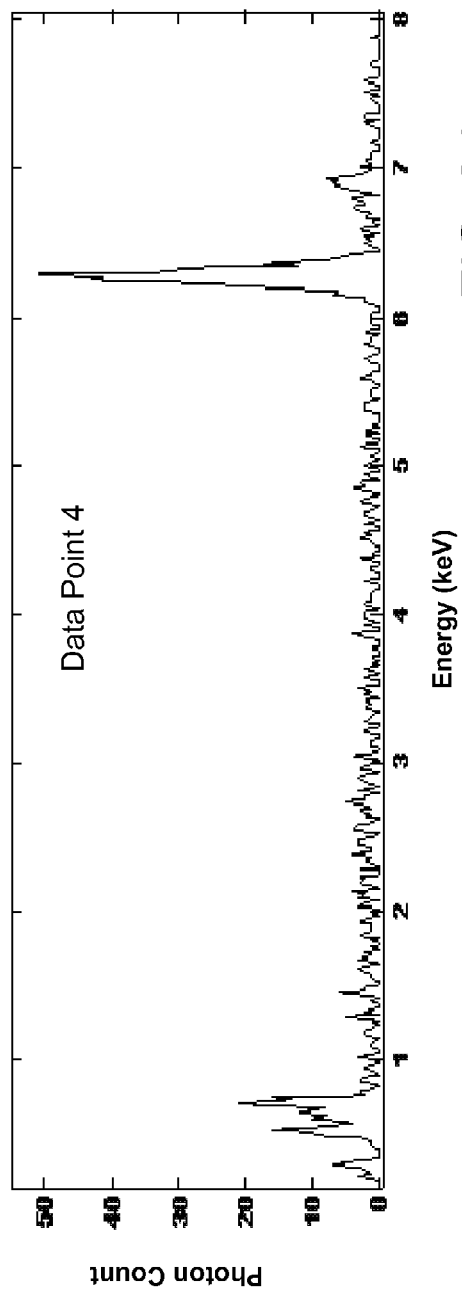
FIG. 3c
FIG. 3d

CLUSTER ANALYSIS OF UNKNOWNS IN SEM-EDS DATASET

TECHNICAL FIELD OF THE INVENTION

The present invention relates generally to methods and structures for identifying minerals using charged particle beam systems and energy dispersive spectroscopy systems.

BACKGROUND OF THE INVENTION

Mineral analysis systems, such as the Qemscan and MLA available from FEI Company, Hillsboro, Oreg., have been used for many years to analyze mineral samples. To determine the type and relative quantity of minerals present in a mine, a sample in the form of small granules, is fixed in epoxy in a mold and the mold is placed in a vacuum chamber. An electron beam is directed toward a sample and, in a process called "energy dispersive x-ray spectroscopy" or "EDS," the energies of x-rays coming from the sample in response to the electron beam are measured and plotted in a histogram to form a spectrum. The measured spectrum can be compared to the known spectra of various elements to determine which elements and minerals are present.

Mineral analysis systems, such as the QEMSCAN® (Quantitative Evaluation of Minerals by Scanning electron microscopy) and MLA (Mineral Liberation Analyzer) from FEI Company, the assignee of the present invention, have been used for many years to determine minerals present in mines in order to determine the presence of valuable minerals. Such systems direct an electron beam toward the sample and measure the energy of x-rays coming from the material in response to the electron beam. One such process is called "energy dispersive x-ray analysis" or "EDS," which can be used for elemental analysis or chemical characterization of a sample. Backscattered electron (BSE) detectors are also used for mineral analysis in conjunction with electron beam columns. The intensity of the BSE signal is a function of the average atomic number of the material under the electron beam, and this relationship can be used to develop a useful mineral identification method.

EDS systems rely on the emission of X-rays from a sample to perform elemental analysis. Each element has a unique atomic structure, which allows x-rays that are characteristic of an element's atomic structure to be uniquely identified from one another. To stimulate the emission of x-rays from a sample, a beam of charged particles is focused onto the sample, which causes electrons from inner shells to be ejected. Electrons from outer shells seek to fill this electron void, and the difference in energy between the higher energy shell and the lower energy shell is released as an x-ray, which can be detected by an EDS detector.

QEMSCAN® comprises a SEM, multiple EDS detectors, and software for controlling automated data acquisition. This technology identifies and quantifies elements within an acquired spectrum and then matches this data against a list of mineral definitions with fixed elemental ranges. The size of the ranges depends directly on the number of x-rays in the spectrum and cannot be applied to higher quality spectra without creating a new mineral definition. Thus, it is not possible to define a universal database for an arbitrary number of X-ray counts. Furthermore, the match is not given as a probability value, it is given as either true or false, and it picks the first match it finds even if a better match might be present elsewhere in the mineral database.

MLA technology also combines a SEM, multiple EDS detectors, and automated quantitative mineralogy software. MLA computes a probability match between a measured mineral spectrum and a reference mineral spectrum. This method works reasonably, but the numerical value obtained tends to be dominated by the size of the largest peak in the x-ray spectrum.

The acquisition time of a suitable BSE signal is typically on the order of microseconds per pixel. However, EDS systems are usually slower and have a longer acquisition time, typically on the order of several seconds per pixel to uniquely discriminate the spectrum from all other mineral spectra. As a result, the time required to collect an x-ray spectrum to uniquely identify a mineral reduces the number of pixels that can be measured substantially. EDS systems are also typically insensitive to light atoms. Because of the advantages of both EDS detectors and BSE detectors, it is sometimes useful to use both BSE and x-ray spectra to accurately identify minerals, which requires more time and becomes a difficult problem to solve with a commercially viable approach.

A mineral classification system must be capable of comparing each unknown measured spectrum to a library of known mineral spectrums, and then making a selection based on which known mineral is most similar to the measured spectrum. Typically, to find the most similar spectrum requires the use of a metric that represents the degree of similarity between the measured data and the known material.

Currently, there are various ways to compare two spectrums directly, either by calculating a distance metric or a similarity metric. An example of a method of comparison used in the prior art is to take the sum of the differences between the two spectrums as a distance. The Mineral Liberation Analyzer manufactured by FEI Company, Inc., the assignee of the present invention, uses a chi-squared statistical test to compare the value at each energy channel of the measured spectrum to the value at the corresponding channel of the known mineral spectrum. These prior art approaches are based around comparing the spectrums on a channel by channel basis. The problem of using a comparison on a channel by channel basis is that there is no guarantee that all required peaks in the mineral spectrum are present in the measured spectrum. It is possible that a measured spectrum appears to be similar to a mineral yet it is missing an element that is required by the definition of that mineral, or has an additional element not found in that definition of a mineral.

In the XBSE_STD measurement mode of the MLA, each data point is compared against a mineral list. If the data point is not similar to any mineral, then a new mineral entry is created and a high quality EDS spectrum is immediately measured from the sample. However, there are several significant limitations of this approach. First, the user is presented with hundreds of unknown data points and there is no way to distinguish which ones occur most frequently and which ones are outliers. Second, the analysis cannot be performed offline as it requires access to the SEM to collect the high quality data during measurement. Finally, only the raw data is presented to the user and there is no analytical tool to give elemental composition. Thus, there is a need for an improved mineral identification method.

SUMMARY OF THE INVENTION

An objection of the invention is to improve the identification of minerals in a sample. The present invention facilitates the determination of the mineral content represented of an SEM-EDS dataset, including initially unknown data points.

SEM-EDS data points are collected and compared to a set of known data points. Any data point that is not sufficiently similar to the known data point is classified as unknown and clustered with like unknown data points. After all data points are analyzed, any clusters of unknown data points with a sufficient number of data points are further analyzed to determine their characteristics.

Embodiments of the invention differentiate unknown data points that are simply outliers, from data points that represent a genuine mineral that is occurring in the sample. The clustering analysis can be performed offline, online, or in real time, and re-processed anytime. The results presented to the operator are typically elemental compositions, average atomic number, or other characteristics that are measured by the analysis. The raw EDS and BSE spectrums may also be presented, as well as the raw data of any other tests done.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which:

FIG. 3a-3j are example spectra obtained by energy dispersive x-ray spectroscopy.

DETAILED DESCRIPTION

Figure 1:
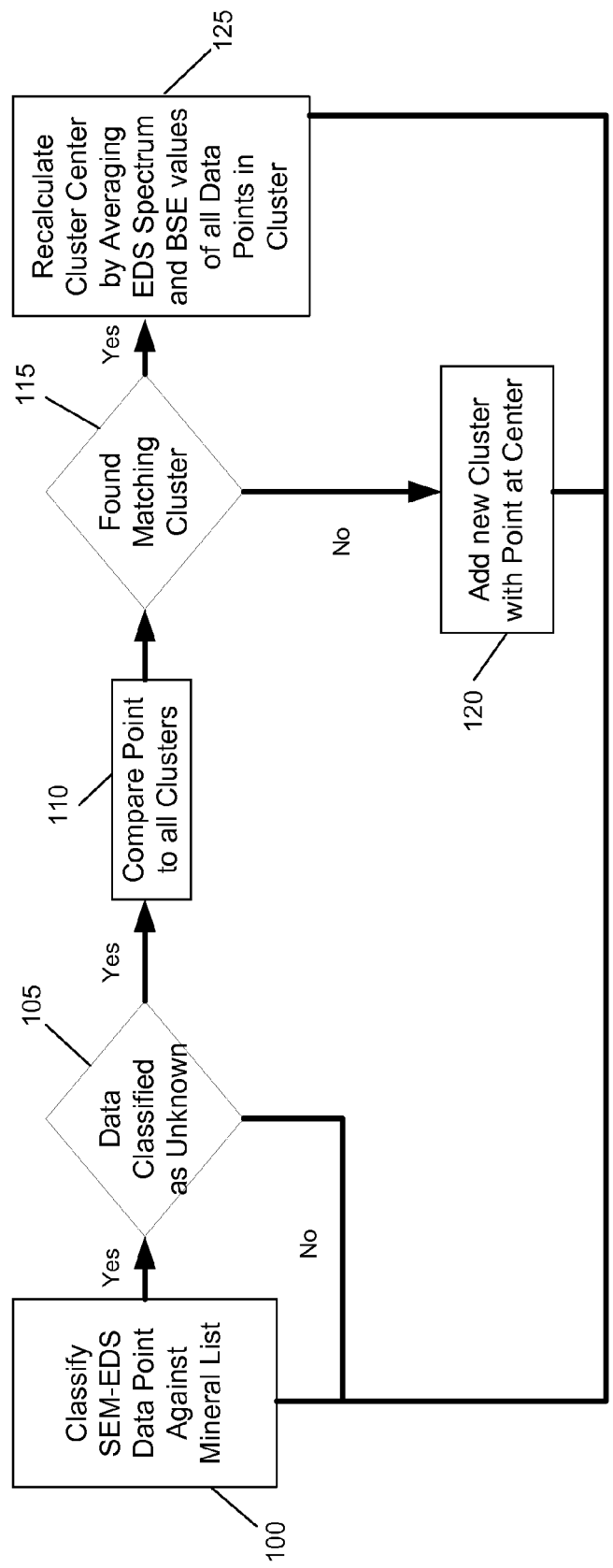
FIG. 1 shows a flow chart of the method to classify all unknown data points into clusters.

Embodiments of the present invention are directed to a method and apparatus for efficiently and easily classifying data points. A "data point" is a group of data, such as an EDS spectrum and/or backscattered electron ("BSE") value. A data point typically corresponds to a mineral. Characteristics of data points corresponding to known minerals are compared to the characteristics of the measured data points. If the characteristics are identical or very similar, the data point is labeled as a known or similar data point. However, if the characteristics of the data point are not similar to the characteristics of the known data points, the data point is labeled as an unknown or dis-similar data point. Any unknown or dis-similar data points will enter into the clustering analysis.

Basic Scanning Technology

A beam is directed toward a sample surface and emissions generated from the surface by the beam impact are detected. The primary beam can comprise, for example, electrons, ions, photons (e.g., a laser beam or x-rays), or atoms. The beam is typically focused to a point on the sample and the point is scanned across the sample. Particles (used herein to include photons and scattered primary particles) that are emitted, backscattered, or transmitted through the sample in response to the primary beam are detected. Different emissions from the sample, such as x-rays, backscattered electrons, secondary electrons, Auger electrons, transmitted electrons, or photons, are detected in various analysis modalities. The invention is not limited to any particular analytical technique.

The different modalities may provide different information about properties of the sample, such as contour information, compositional information, topographical information, or chemical state information. For example, backscattered electron data may be acquired at the same time as x-ray data, with the x-rays being placed at the correct location in the backscattered electron image to produce a spectrum cube. In some embodiments, the different analysis modalities include detecting emissions generated by different beams at different times.

In some embodiments, an electron beam is directed toward a sample and scanned across regions having different characteristics, such as different mineral compositions. A first detector may provide information about contour, topography, or atomic number, for example, by detecting backscattered electrons, while a second detector may provide information about composition, for example, by detecting characteristic x-rays.

Clustering

Cluster analysis, or clustering, is the task of assigning a set of objects into groups, also called clusters, so that the objects in the same cluster are more similar to each other than to those in other clusters. Cluster analysis groups objects based on the information found in the data describing the objects or their relationships. The goal is that the objects in a group will be similar to one other and different from the objects in other groups. The greater the similarity within a group, and the greater the difference between groups, the "better" or more distinct the clustering.

Cluster analysis itself is not one specific algorithm, but is an general approach to assigning minerals identifications. It can be achieved by various algorithms that differ significantly in their notion of what constitutes a cluster and how to efficiently find them. Clustering can therefore be formulated as a multi-objective optimization problem. The appropriate clustering algorithm and parameter settings, including values such as the distance function to use, a density threshold or the number of expected clusters, depend on the individual data set and intended use of the results. Cluster analysis is typically an iterative process of knowledge discovery or interactive multi-objective optimization that involves trial and error. It will often be necessary to modify preprocessing and parameters until the result achieves the desired properties.

Any standard clustering technique, such as Agglomerative, Single-Pass or K-Means, may be used for the analysis of the present invention. For example, one possible distance metric takes the sum of the differences between the EDS Spectrum channel values.

As shown in FIG. 1, the first step in the process is to classify every data point in the SEM-EDS data set, 100, as a known or unknown, 105. A data point is "known" if its spectrum matches the known spectrum of a mineral within a predetermined limit. For example, one measurement of how well spectra match is the Cosine Similarity metric analysis as given in Equation 1.

$$\text{similarity} = \cos(\theta) = \frac{A \cdot B}{\|A\|\|B\|} = \frac{\sum_{i=1}^{n} A_i \times B_i}{\sqrt{\sum_{i=1}^{n} (A_i)^2} \times \sqrt{\sum_{i=1}^{n} (B_i)^2}} \quad \text{Equation (1)}$$

Where "i" represents each measurement parameter, such as each normalized energy channel height, average atomic number from back-scattered electron analysis, or other measurement parameter, and the values of data point each spectrum are summed over all the energy channels and other measurements. In some embodiments, a spectrum is considered a match to a reference spectrum when the similarity metric of the two is greater than 90%.

After excluding known data points, all unknown data points are compared to the clusters of unknown data points, 110. If the unknown data point's characteristics are similar to another cluster, that is, the similarity metric is greater than a pre-determined amount, the unknown data point is placed in that cluster, 115. If the unknown data point is not similar to other clusters, a new cluster is created, 120. The average value of every cluster for each energy channel is recalculated after the addition of each new data point to further refine the cluster's characteristics and differentiate each cluster from the others, 125.

Figure 2:
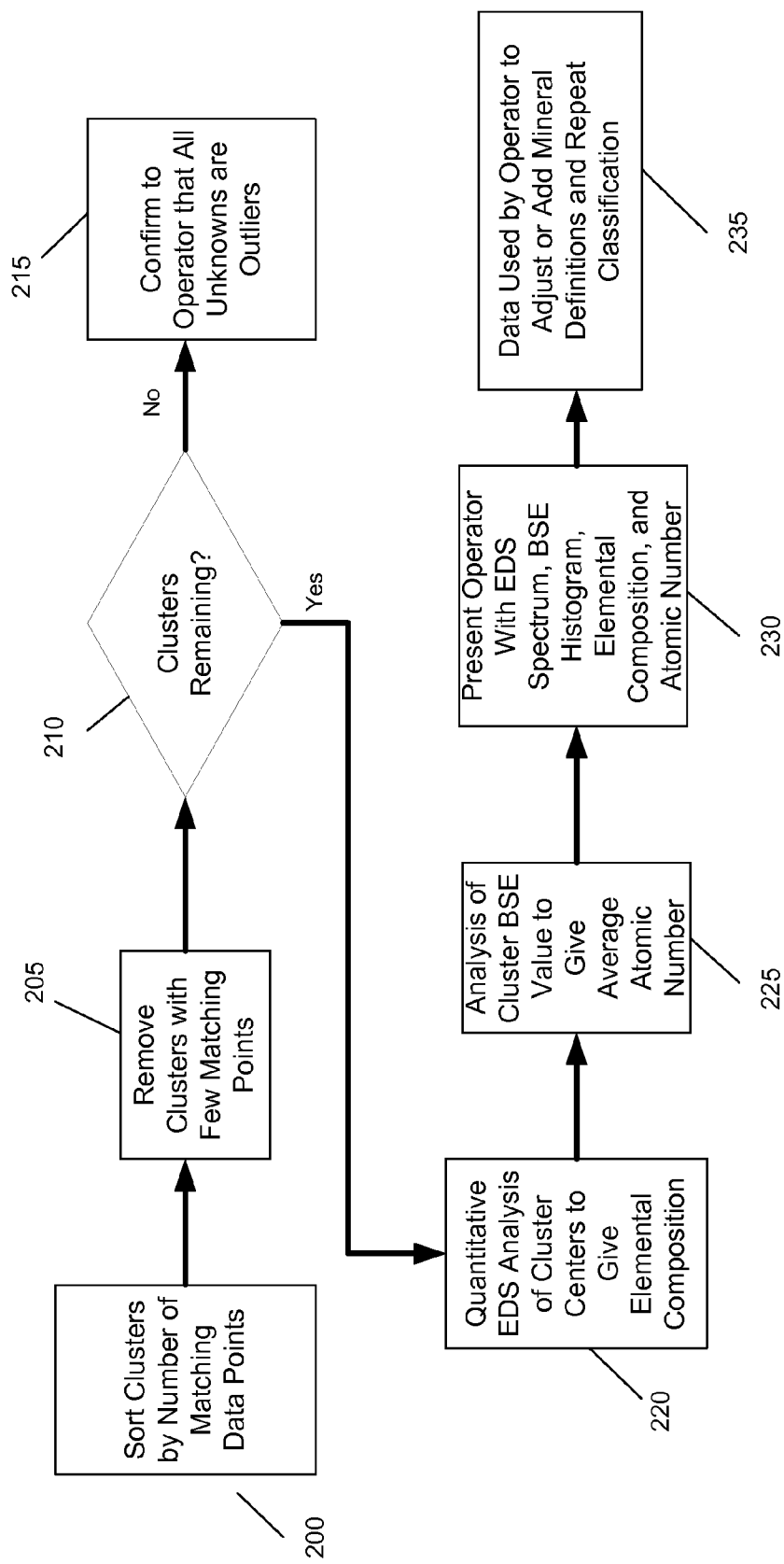
FIG. 2 shows the analysis of all clusters to determine if they contain only outlier data points or if the mineral definition list needs updating.
Figure 3A:
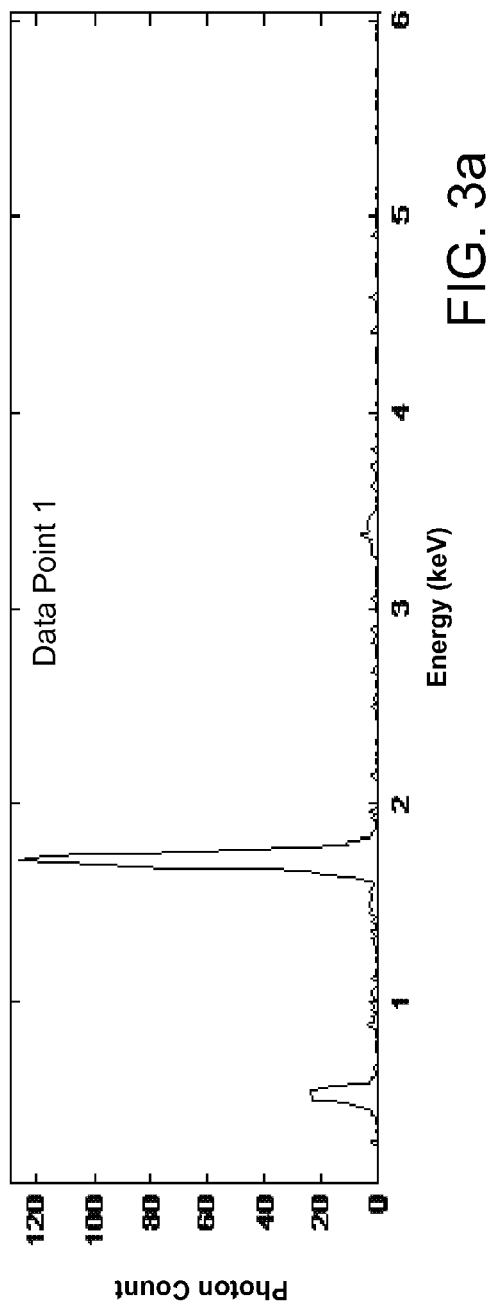
Figure 3B:
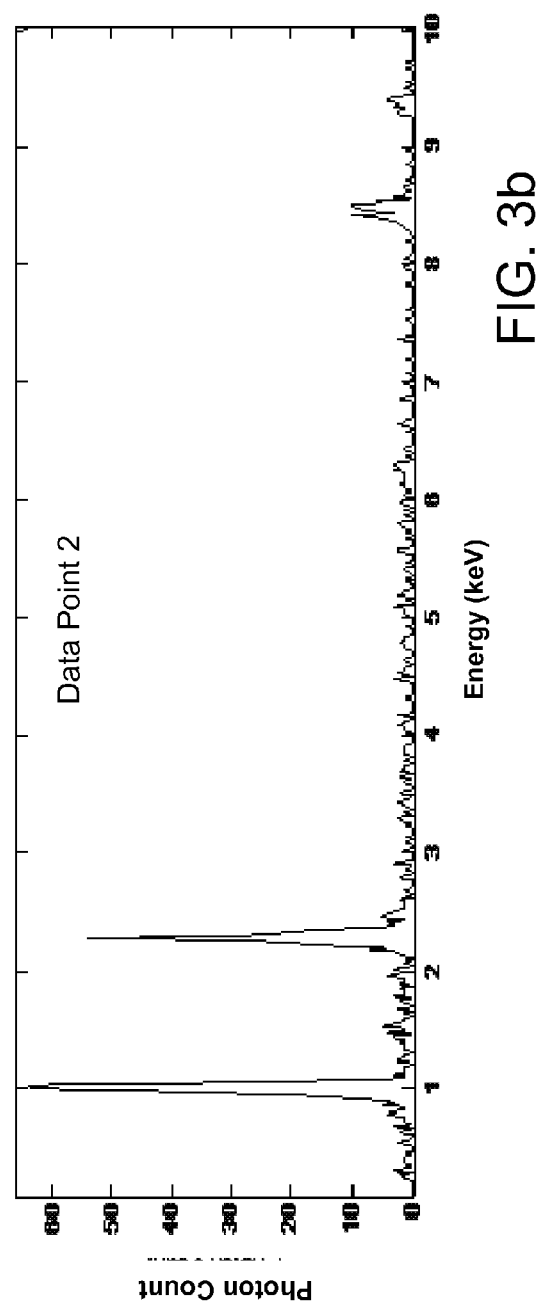
Figure 3E:
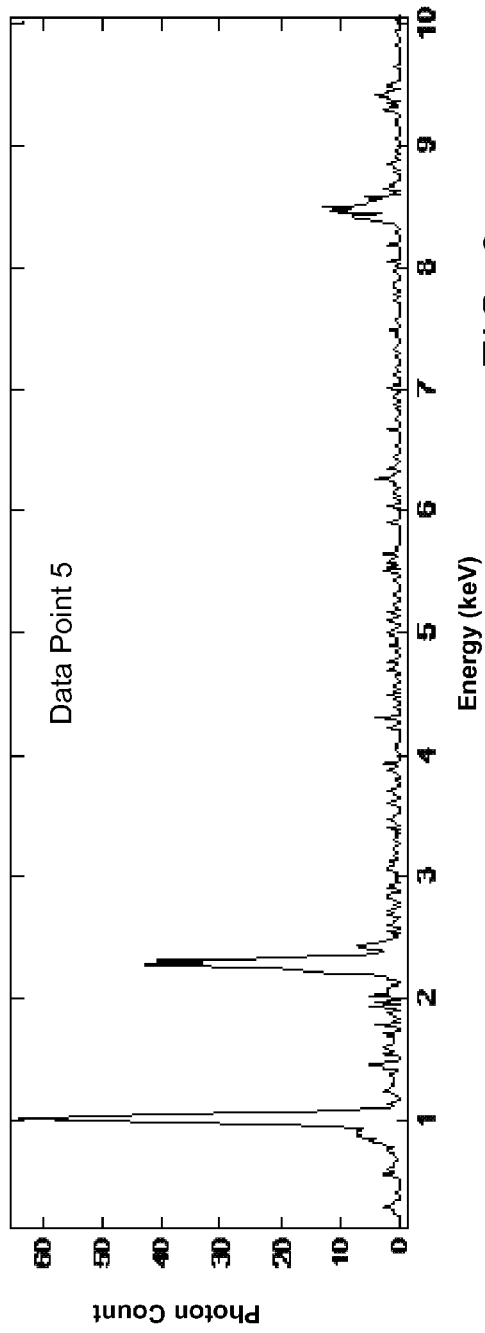
Figure 3F:
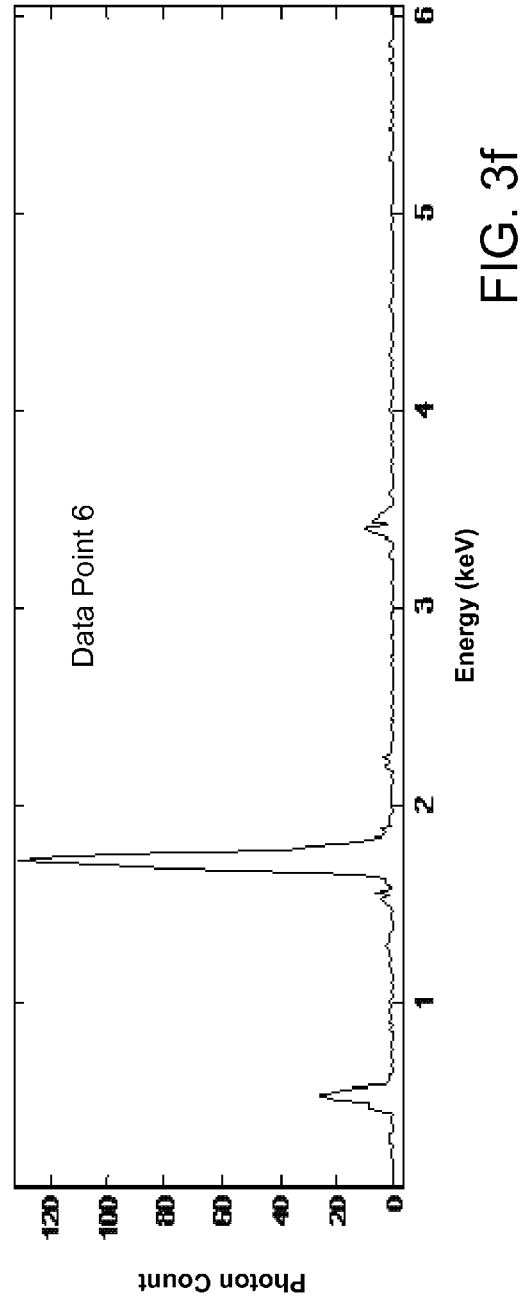
Figures 3G, 3H:
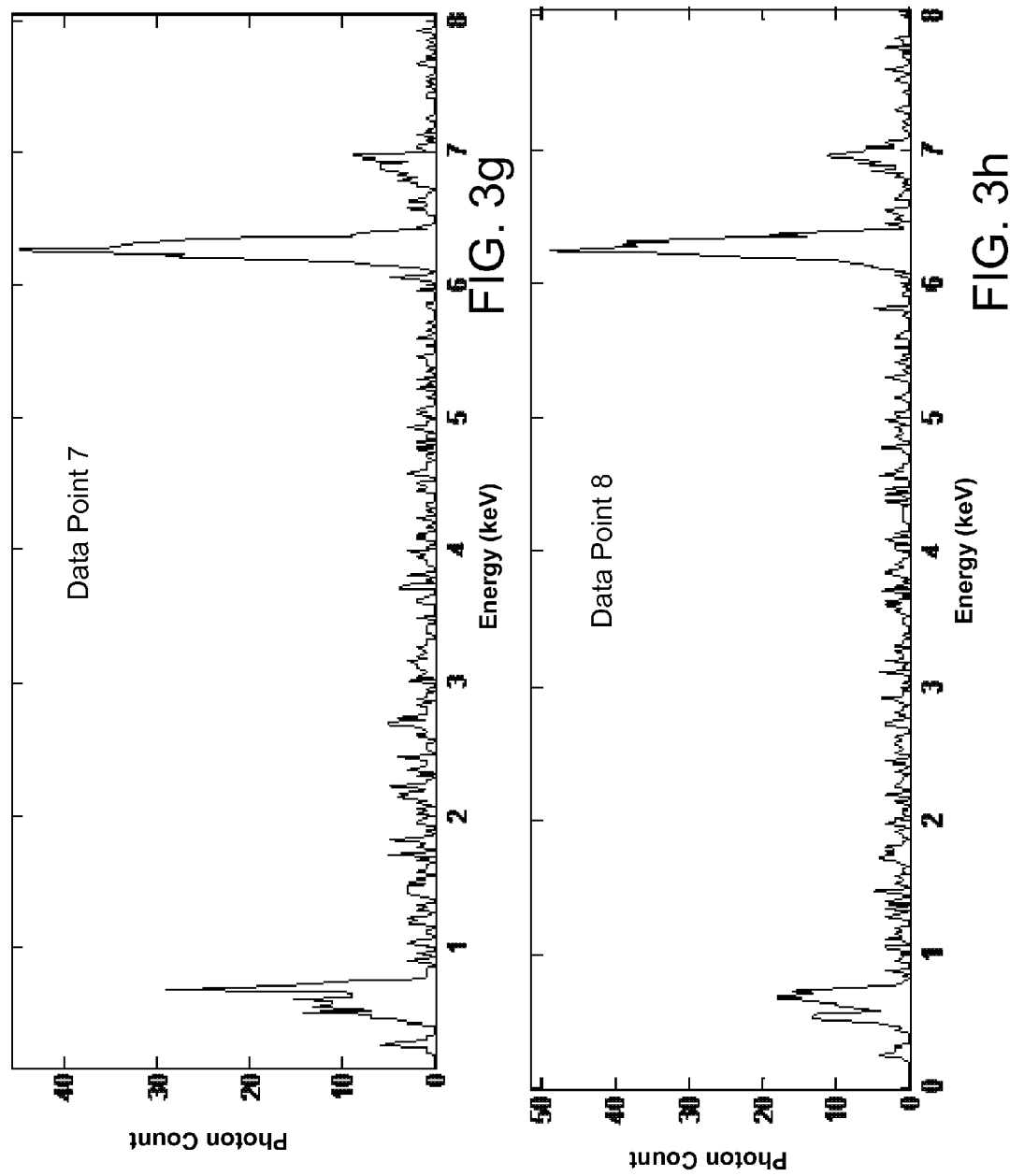
Figure 3I:
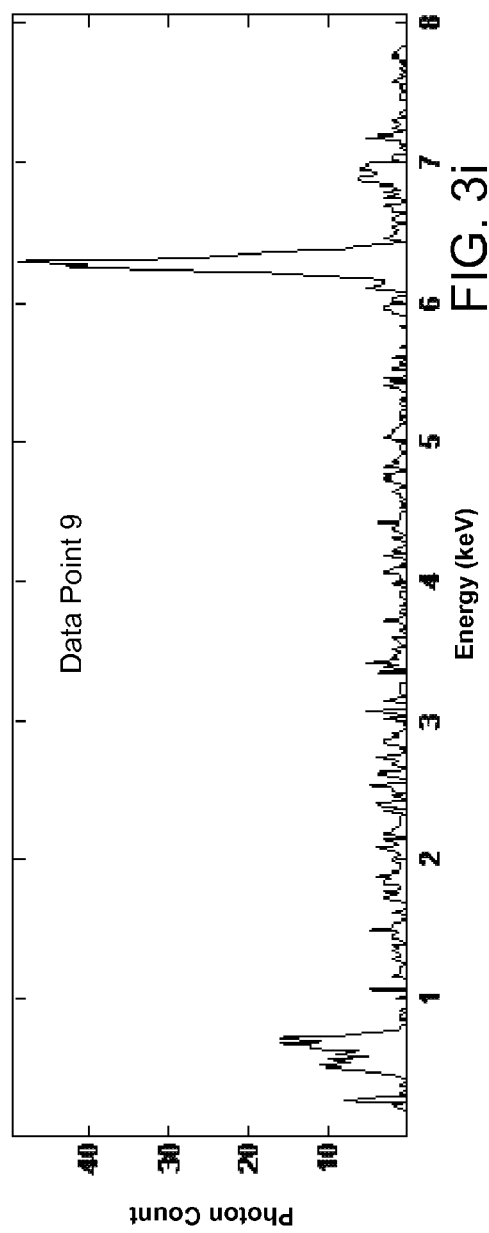
Figure 3J:
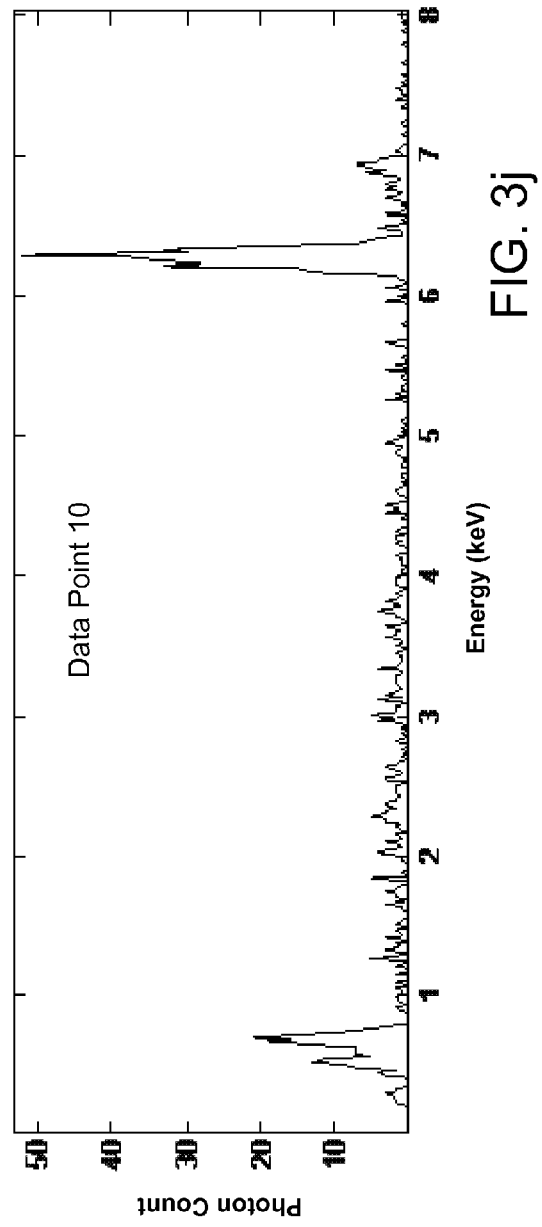

The results of the clustering analysis will be several clusters, with each cluster containing least one "unknown" data point. As shown in FIG. 2., once the SEM-EDS data set is reduced to known data points and clusters of unknown data points, the clusters are sorted by the number of data points in the clusters, 200. This list can be reduced to only those clusters that matched a significant number of data points, 205, for example the top 20 clusters, although analysis of all or fewer clusters is possible. As used herein matching means unknown data points are clustered or grouped together when the characteristics of each data point are identical or similar to the characteristics of the other data points in the cluster or group. In one embodiment, the characteristics of each data point in a group should be within at least three percent of the average value of the all data points in the group. The matching criteria can be tightened if more precise measurements are needed.

Once all clusters have been sorted, it is determined whether or not there are any clusters remaining, 210. If there are no clusters remaining after removal of those with few data points, the remaining clusters are outliers, 215, and the process is complete.

However, if there are clusters remaining, it means that there is a mineral in the sample that has not been identified. The remaining clusters then undergo quantitative EDS analysis to give the elemental composition of the unknown minerals, 220, and a BSE analysis to determine the average atomic number of the minerals, 225. The average EDS spectrum and BSE value is calculated from each cluster, by averaging all the data points within a cluster. This gives a high quality EDS spectrum that can be further analyzed to give accurate elemental composition and atomic numbers based on BSE data.

Once all data is analyzed and placed in the appropriate cluster, the analyzed cluster data is presented to the operator, 230, who may make use of the data to expand the list of mineral definitions to minimize the unknown data points, 235, eliminate clusters with minimal data points, 205, and/or determine that all "unknown" data points are outliers and can be ignored, 215. If desired the operator can instruct the analysis to be repeated so as to rerun the sample with and updated known data point list which will produce fewer unknown data points.

EXAMPLE

Figure 4A:
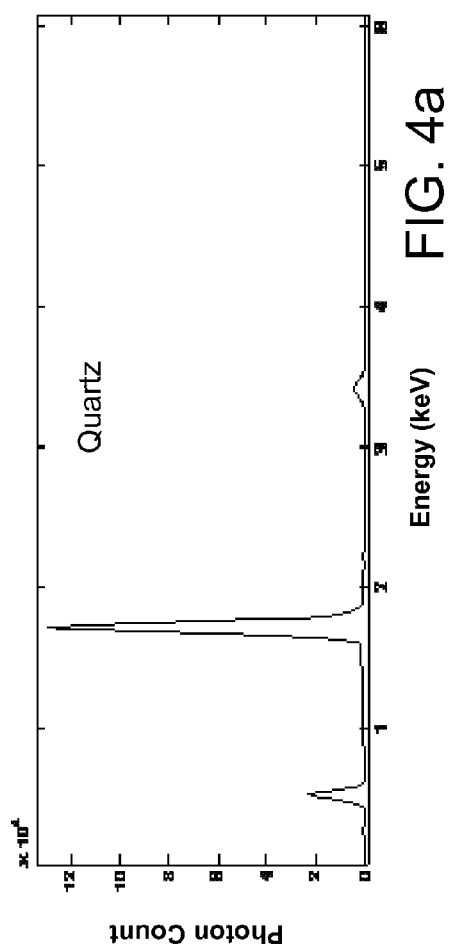
FIGS. 4B and 4B are x-ray spectra of quartz and pyrite, respectively.
Figure 4B:
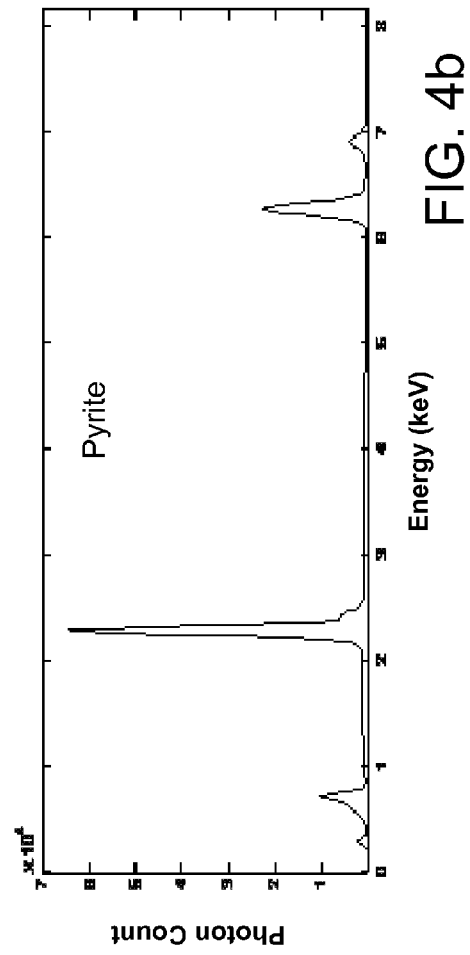

The following example shows an analysis of 10 different samples having spectra show in FIGS. 3a-3j. The spectra of the ten samples are being compared to spectra of known minerals in a mineral list. In this example, the mineral list has only two minerals, quartz and pyrite, having spectra as shown in FIGS. 4a and 4b. Each of the spectra of a sample represents a data point. In this example, the data point does not include back scattered electron data. After obtaining the spectra corresponding to the ten points, each data point is analyzed for its similarities with known spectra, for example, by using a cosine comparison on multiple energy channels. Table 1 shows the results of the comparison, and the classification shows how the result of the analysis.

In this example the known data points are Quartz and Pyrite.

TABLE 1

Sample Data and Cluster Analysis

| Number | Similarity With Quartz | Similarity With Pyrite | Similarity with Unknown_1 | Similarity with Unknown_2 | Classification |
|---|---|---|---|---|---|
| 1 | 99.2% | 4.3% | — | — | Identified as quartz |
| 2 | 3.73% | 54.19% | — | — | New cluster added 'Unknown_1' |
| 3 | 3.04% | 98.18% | — | — | Identified as Pyrite |
| 4 | 5.77% | 43.08% | 8.63% | | New Cluster added 'Unknown_2' |
| 5 | 4.54% | 47.81% | 95.37% | 10.43% | Matches cluster 'Unknown_1' |
| 6 | 98.96% | 4.7% | 4.16% | 7.22% | Identified as Quartz |
| 7 | 6.45% | 44.89% | 10.72% | 91.70% | Matches cluster 'Unknown_2' |
| 8 | 8.96% | 43.72% | 11.03% | 92.81% | Matches cluster 'Unknown_2' |
| 9 | 6.02% | 43.03% | 11.67% | 92.42% | Matches cluster 'Unknown_2' |
| 10 | 9.04% | 43.93% | 11.45% | 93.16% | Matches cluster 'Unknown_2' |

In this example, a spectrum is considered a match when the similarity between samples is greater than ninety percent (90%). As seen in Table 1, samples 1 and 6 have a 99.2% match and 98.96% match respectively with the known values of Quartz, thus the software will designate those samples as Quartz. Sample 2 does not match with either Quartz or Pyrite to a degree of greater than 90%, so it is classified as an unknown sample and place in unknown cluster one. Sample 3 has a match of 98.18% with the known value of Pyrite, thus the software will classify this sample as Pyrite. Sample 4 does not match any of the known samples, and does not match closely with the first unknown sample, sample 3, so it is classified as a second unknown sample and placed in unknown cluster two. Sample 5 has a greater than 90% match to Sample 2 and is placed in unknown cluster one. Samples 7-10 have a greater than 90% match to sample 4, therefore these samples are placed in unknown cluster two. At this point the operator can evaluate the samples in unknown clusters one and two to determine if further analysis is needed, additional known data sets should be added to the software, or if the unknown clusters are simply outlier data points that can be ignored. Thus it can be seen that the current method can quickly and easily cluster unknown samples for more efficient handling.

Figure 5:
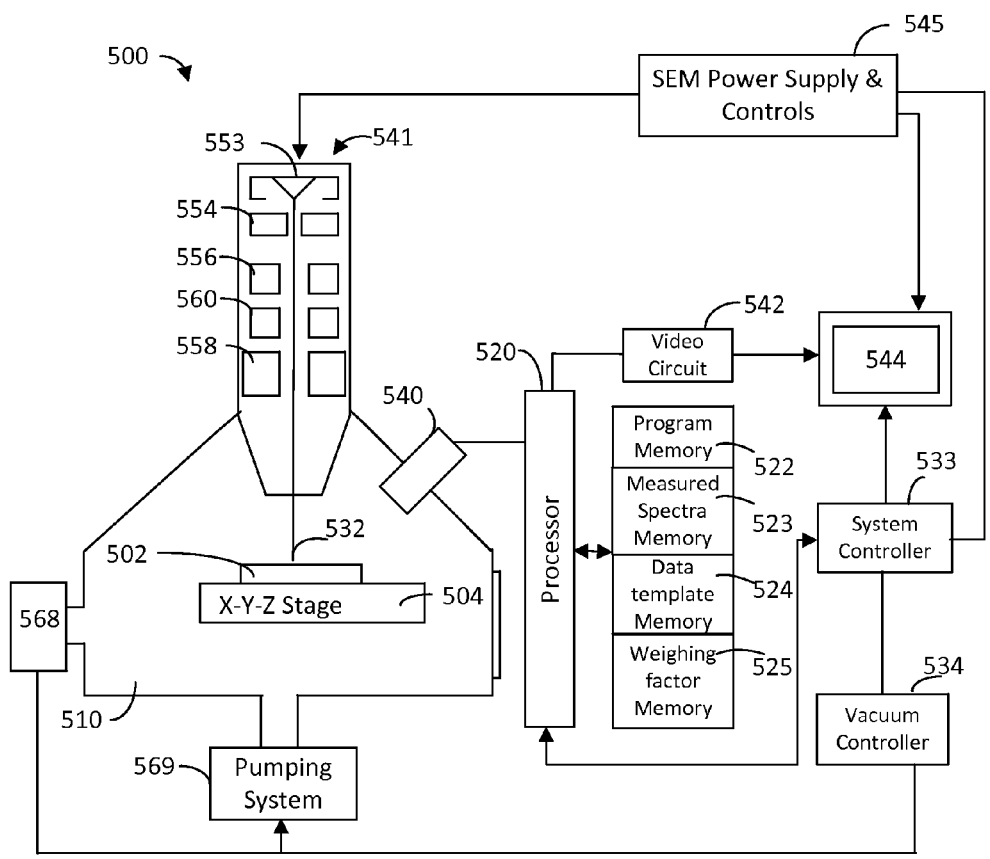
FIG. 5 is a scanning electron microscope system with EDS capability.

FIG. 5 is an example of a scanning electron beam system 500 with an x-ray detector 540 suitable for analyzing samples prepared according to the present invention. A scanning electron microscope 541, along with power supply and control unit 545, is provided with system 500. An electron beam 532 is emitted from a cathode 553 by applying voltage between cathode 553 and an anode 554. Electron beam 532 is focused to a fine spot by means of a condensing lens 556 and an objective lens 558. Electron beam 532 is scanned two-dimensionally on the specimen by means of a deflection coil 560. Operation of condensing lens 556, objective lens 558, and deflection coil 560 is controlled by power supply and control unit 545.

A system controller 533 controls the operations of the various parts of scanning electron beam system 500. The vacuum chamber 510 is evacuated with ion pump 568 and mechanical pumping system 569 under the control of vacuum controller 534.

Electron beam 532 can be focused onto sample 502, which is on movable X-Y stage 504 within lower vacuum chamber 510. When the electrons in the electron beam strike sample 502, the sample gives off x-rays whose energy correlated to the elements in the sample. X-rays (not shown) have energy inherent to the elemental composition of the sample are produced in the vicinity of the electron beam incident region. Emitted x-rays are collected by x-ray detector 540, preferably an energy dispersive detector of the silicon drift detector type, although other types of detectors could be employed, which generates a signal having an amplitude proportional to the energy of the detected x-ray.

Output from detector 540 is amplified and sorted by the processor 520, which counts and sorts the total number of X-rays detected during a specified period of time, at a selected energy and energy resolution, and a channel width (energy range) of preferably between 10-20 eV per channel. Processor 520 can comprise a computer processor; operator interface means (such as a keyboard or computer mouse); program memory 522 for storing data and executable instructions; interface means for data input and output, executable software instructions embodied in executable computer program code; and display 544 for displaying the results of a multivariate spectral analysis by way of video circuit 542.

Processor 520 can be a part of a standard laboratory personal computer, and is typically coupled to at least some form of computer-readable media. Computer-readable media, which include both volatile and nonvolatile media, removable and non-removable media, may be any available medium that can be accessed by processor 520. By way of example and not limitation, computer-readable media comprise computer storage media and communication media. Computer storage media include volatile and nonvolatile, removable and non-removable media implemented in any method or technology for storage of information such as computer-readable instructions, data structures, program modules or other data. For example, computer storage media include RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that can be used to store the desired information and that can be accessed by processor 520.

Program memory 522 can include computer storage media in the form of removable and/or non-removable, volatile and/or nonvolatile memory and can provide storage of computer-readable instructions, data structures, program modules and other data. Generally, the processor 520 is programmed by means of instructions stored at different times in the various computer-readable storage media of the computer. Programs and operating systems are typically distributed, for example, on floppy disks or CD-ROMs. From there, they are installed or loaded into the secondary memory of a computer. At execution, they are loaded at least partially into the computer's primary electronic memory. The invention described herein includes these and other various types of computer-readable storage media when such media contain instructions or programs for implementing the steps described below in conjunction with a microprocessor or other data processor. The invention also includes the computer itself when programmed according to the methods and techniques described herein.

An x-ray spectrum obtained as described above can be stored in a portion of memory 522, such as the measured spectra memory portion 523. Data template memory portion 524 stores data templates, such as definitions of known spectra of elements or, in some embodiments, known diffraction patterns of materials. A weighing factor memory 525 stores weighing factors.

While the embodiment shown includes a scanning electron microscope, related embodiment could use a transmission electron microscope or a scanning transmission electron microscope to generate x-rays from the sample. An x-ray fluorescence system could also be used to generate x-rays from the sample. Other embodiments may detect other characteristic radiation, such as gamma rays, from a sample.

Further, whenever the terms "automatic," "automated," or similar terms are used herein, those terms will be understood to include manual initiation of the automatic or automated process or step. Whenever a scan or image is being processed automatically using computer processing, it should be understood that the raw image data can be processed without ever generating an actual viewable image. In the following discussion and in the claims, the terms "including" and "comprising" are used in an open-ended fashion, and thus should be interpreted to mean "including, but not limited to . . . "

It should be recognized that embodiments of the present invention can be implemented via computer hardware or software, or a combination of both. The methods can be implemented in computer programs using standard programming techniques—including a computer-readable storage medium configured with a computer program, where the storage medium so configured causes a computer to operate in a specific and predefined manner—according to the methods and figures described in this specification. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits programmed for that purpose.

Further, methodologies may be implemented in any type of computing platform, including but not limited to, personal computers, mini-computers, main-frames, workstations, networked or distributed computing environments, computer platforms separate, integral to, or in communication with charged particle tools or other imaging devices, sensors, and the like. Aspects of the present invention may be implemented in machine readable code stored as memory on a storage medium or device, whether removable or integral to the computing platform, such as a hard disc, optical read and/or write storage mediums, RAM, ROM, and the like, so that it is readable by a programmable computer, for configuring and operating the computer when the storage media or device is read by the computer to perform the procedures described herein. Moreover, machine-readable code, or portions thereof, may be transmitted over a wired or wireless network. The invention described herein includes these and other various types of computer-readable storage media when such media contain instructions or programs for implementing the steps described above in conjunction with a microprocessor or other data processor. The invention also includes the computer itself when programmed according to the methods and techniques described herein.

Computer programs can be applied to input data to perform the functions described herein and thereby transform the input data to generate output data. The output information is applied to one or more output devices such as aberration correctors or to a display monitor. In preferred embodiments of the present invention, the transformed data represents physical and tangible objects, including producing a particular visual depiction of the physical and tangible objects on a display.

Preferred embodiments of the present invention may make use of a particle beam apparatus, energy beam apparatus, or apparatus using a physical probe tip in order to image a sample. Such beams or physical probes used to image a sample inherently interact with the sample resulting in some degree of physical transformation. Further, throughout the present specification, discussions utilizing terms such as "calculating," "determining," "measuring," "generating," "detecting," "forming," "resetting," "reading," "subtracting," "detecting," "comparing," "acquiring," "mapping," "recording," "transforming," "changing," or the like, also refer to the action and processes of a computer system, a sensor, or similar electronic device, that manipulates and transforms data represented as physical quantities within the computer system into other data similarly represented as physical quantities within the computer system or other information storage, transmission or display devices.

The invention has broad applicability and can provide many benefits as described and shown in the examples above. The embodiments will vary greatly depending upon the specific application, and not every embodiment will provide all of the benefits and meet all of the objectives that are achievable by the invention. Particle beam systems suitable for carrying out some embodiments of the present invention are commercially available, for example, from FEI Company, the assignee of the present application.

To the extent that any term is not specially defined in this specification, the intent is that the term is to be given its plain and ordinary meaning. The accompanying drawings are intended to aid in understanding the present invention and, unless otherwise indicated, are not drawn to scale. Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method for determining the mineral content of a sample, said method comprising:
   directing an electron beam toward multiple point of unknown composition;
   detecting x-rays emitted as a result of the electron beam impacting the sample to acquire an a-ray spectrum, and forming a data point;
   classifying the data point from a sample by comparison to a set of known data points as a classified data point, wherein said classified data point is classified as a similar data point if the characteristics of the classified data point are similar to the characteristics of a known data point and alternatively the classified data point is classified as a dis-similar data point if the characteristics of the classified data point are not similar to that of a known data point;
   placing the data point into a group wherein the characteristics of the data points within the group have characteristics similar to that of the classified data point;
   repeating the previous steps until all data points are classified data points and are placed in groups with similar characteristics; and
   analyzing the groups with dis-similar data points to for use in processing the mineral sample.

2. The method of claim 1, further comprising: removing all groups of dis-similar data points except twenty groups with the most number of dis-similar data points before analyzing the groups with dis-similar data points to determine the mineral content of the groups with dis-similar data points.

3. The method of claim 1, further comprising removing all groups of dis-similar data points with five or less dis-similar data points before analyzing the groups with dis-similar data points to determine the mineral content of the groups with dis-similar data points.

4. The method of claim 1, further comprising removing all groups of dis-similar data points with twenty or less dis-similar data points before analyzing the groups with dis-similar data points to determine the mineral content of the groups with dis-similar data points.

5. The method of claim 1 wherein the groups with dis-similar data points are analyzed to determine the mineral content of the groups with dis-similar data points by conducting a quantitative energy dispersive x-ray spectroscopy to determine an elemental composition of the group of dissimilar data points.

6. The method of claim 5 wherein the set of known data points are altered based on the results of the energy dispersive x-ray spectroscopy analysis and the sample is processed again with the altered set of known data points.

7. The method of claim 1 wherein the groups with dissimilar data points are analyzed to determine the average atomic number of the groups with dis-similar data points by conducting a backscattered electron detector analysis.

8. The method of claim 7 wherein the set of known data points are altered based on the results of the back-scattered electron detector analysis and the sample is processed again with the altered set of known data points.

9. The method of claim 1 wherein each group of classified data points has an average value which is recalculated with the addition of each classified data point.

10. The method of claim 9 wherein the characteristic of each classified data point is within three percent of the average characteristic value of the group it is placed in.

11. The method of claim 9 wherein the characteristic of each classified data point is within one percent of the average characteristic value of the group it is placed in.

12. The method of claim 9 wherein the characteristic of each classified data point is within 0.01 percent of the average characteristic value of the group it is placed in.

13. The method of claim 1 wherein a newly classified data point is placed in a separate group if there are no previously classified data points with characteristics similar to the newly classified data points.

14. A scanning electron microscope x-ray spectroscopy device comprising:
- a source of a charged particle beam or photon beam and means for directing the beam towards a mineral sample;
- a detector for detecting emissions from the sample in response to the beam and for forming a data set comprising multiple data points;
- a processor for controlling the scanning electron microscope; and
- a computer readable data storage storing computer instruction to:
- classify an x-ray spectroscopy data point taken from the sample by comparison to a set of known data points as a classified data point wherein said classified data point is classified as a similar data point if the characteristics of the classified data point are similar to the characteristics of a known data point and alternatively the classified data point is classified as a dis-similar data point if the characteristics of the classified data point are not similar to that of a known data point;
- place the x-ray spectroscopy data point into a group wherein the characteristics of the data points within the group have characteristics similar to that of the classified data point;
- repeat the previous steps until all x-ray spectroscopy data points are classified data points and are placed in groups with similar characteristics;
- analyze the groups with dis-similar data points to for use in processing the mineral sample.

* * * * *